US008609373B2

(12) United States Patent
Liu et al.

(10) Patent No.: US 8,609,373 B2
(45) Date of Patent: Dec. 17, 2013

(54) FUSION PROTEIN MIXTURE FOR INDUCING HUMAN PLURIPOTENT STEM CELL AND PREPARATION METHOD THERE OF

(75) Inventors: Chen Liu, Shanghai (CN); Lijun Cai, Shanghai (CN); Jianfeng Ding, Shanghai (CN)

(73) Assignee: Novoprotein Scientific (Shanghai) Inc., Shanghai (CN)

( * ) Notice: Subject to any disclaimer, the term of this patent is extended or adjusted under 35 U.S.C. 154(b) by 0 days.

(21) Appl. No.: 13/389,884

(22) PCT Filed: Aug. 12, 2010

(86) PCT No.: PCT/CN2010/001223
§ 371 (c)(1),
(2), (4) Date: Feb. 10, 2012

(87) PCT Pub. No.: WO2011/017910
PCT Pub. Date: Feb. 17, 2011

(65) Prior Publication Data
US 2012/0196328 A1 Aug. 2, 2012

(30) Foreign Application Priority Data
Aug. 12, 2009 (CN) .......................... 2009 1 0057744

(51) Int. Cl.
*C12P 21/02* (2006.01)
*C07K 19/00* (2006.01)
*C07K 14/00* (2006.01)
*A61K 38/16* (2006.01)

(52) U.S. Cl.
USPC .......... 435/69.7; 435/366; 530/350; 514/21.2

(58) Field of Classification Search
None
See application file for complete search history.

(56) References Cited

U.S. PATENT DOCUMENTS

| 6,872,551 B2 * | 3/2005 | Lima et al. ................... 435/69.7 |
| 2004/0029281 A1 * | 2/2004 | Joliot et al. ................... 435/456 |
| 2009/0068742 A1 * | 3/2009 | Yamanaka ................... 435/455 |

FOREIGN PATENT DOCUMENTS

| CN | 101250502 A | 8/2008 |
| CN | 101356270 A | 1/2009 |
| WO | 2009/057831 A1 | 5/2009 |

OTHER PUBLICATIONS

Vitte Al et al. Intracellular delivery of peptides via association with ubiquitin or SUMO-1 coupled to protein transduction domains. 2008. BMC Biotechnology. 8:24 1-11.*
Arenzana-Seisdedos F et al. Nuclear localization of IkBa promotes active transport of NF-kB from the nucleus to the cytoplasm. 1997. Journal of Cell Science. 110:369-378.*
Takahashi K et al., Induction of Pluripotent Stem Cells From Adult Human Fibroblasts by Defined Factors. Cell, Nov. 30, 2007, vol. 131, No. 5, pp. 861-871.
PCT International Search Report dated Nov. 25, 2010; (PCT/CN2010/001223).

* cited by examiner

*Primary Examiner* — David J Steadman
*Assistant Examiner* — Paul Holland
(74) *Attorney, Agent, or Firm* — MKG, LLC

(57) ABSTRACT

The invention provides the protein mixture including the fusion proteins of C-myc, SOX2, KLF4, OCT-4, wherein each protein comprises a protein transduction domain (PTD) and a small ubiquitin-like modifier (SUMO) fused with the said protein. The invention further provides the preparation method of the protein mixture and its use for inducing human pluripotent stem cell.

8 Claims, 3 Drawing Sheets

SEQUENCE LISTING

<160> NUMBER OF SEQ ID NOS: 28

<210> SEQ ID NO 1
<211> LENGTH: 381
<212> TYPE: DNA
<213> ORGANISM: artificial sequence
<220> FEATURE:
<223> OTHER INFORMATION: synthetic

<400> SEQUENCE: 1

```
tacggtcgta aaaaacgtcg tcagcgtcgt cgtatgggtc atcaccatca tcatcacatg      60
gtgaaagaac tgcaggaaat tcgtctgggg tcggactcag aagtcaatca agaagctaag     120
ccagaggtca agccagaagt caagcctgag actcacatca atttaaaggt gtccgatgga     180
tcttcagaga tcttcttcaa gatcaaaaag accactcctt taagaaggct gatggaagcg     240
ttcgctaaaa gacagggtaa ggaaatggac tccttaagat tcttgtacga cggtattaga     300
attcaagctg atcaggcccc tgaagatttg gacatggagg ataacgatat tattgaggct     360
catcgcgaac agattggagg t                                               381
```

<210> SEQ ID NO 2
<211> LENGTH: 128
<212> TYPE: PRT
<213> ORGANISM: artificial sequence
<220> FEATURE:
<223> OTHER INFORMATION: synthetic

<400> SEQUENCE: 2

Met Tyr Gly Arg Lys Lys Arg Arg Gln Arg Arg Met Gly His His
1               5                   10                  15

His His His His Met Val Lys Glu Leu Gln Glu Ile Arg Leu Gly Ser
            20                  25                  30

Asp Ser Glu Val Asn Gln Glu Ala Lys Pro Glu Val Lys Pro Glu Val
        35                  40                  45

Lys Pro Glu Thr His Ile Asn Leu Lys Val Ser Asp Gly Ser Ser Glu
    50                  55                  60

Ile Phe Phe Lys Ile Lys Lys Thr Thr Pro Leu Arg Arg Leu Met Glu
65                  70                  75                  80

Ala Phe Ala Lys Arg Gln Gly Lys Glu Met Asp Ser Leu Arg Phe Leu
                85                  90                  95

Tyr Asp Gly Ile Arg Ile Gln Ala Asp Gln Ala Pro Glu Asp Leu Asp
            100                 105                 110

Met Glu Asp Asn Asp Ile Ile Glu Ala His Arg Glu Gln Ile Gly Gly
        115                 120                 125

<210> SEQ ID NO 3
<211> LENGTH: 1338
<212> TYPE: DNA
<213> ORGANISM: artificial sequence
<220> FEATURE:
<223> OTHER INFORMATION: synthetic

<400> SEQUENCE: 3

```
atgtacggtc gtaaaaaacg tcgtcagcgt cgtcgtatgg gtcatcacca tcatcatcac    60
atggtgaaag aactgcagga aattcgtctg ggtcggact  cagaagtcaa tcaagaagct   120
aagccagagg tcaagccaga agtcaagcct gagactcaca tcaatttaaa ggtgtccgat   180
ggatcttcag agatcttctt caagatcaaa aagaccactc ctttaagaag gctgatggaa   240
gcgttcgcta aaagacaggg taaggaaatg gactccttaa gattcttgta cgacggtatt   300
agaattcaag ctgatcaggc ccctgaagat ttggacatgg aggataacga tattattgag   360
gctcatcgcg aacagattgg aggtatgtac aacatgatgg agacggagct gaagccgccg   420
ggccccgcagc aaacttcggg gggcggcggc ggcaactcca ccgcggcggc ggccggcggc   480
aaccagaaaa acagcccgga ccgcgtcaag cggcccatga atgccttcat ggtgtggtcc   540
cgcgggcagc ggcgcaagat ggcccaggag aacccccaaga tgcacaactc ggagatcagc   600
aagcgcctgg cgccgagtg gaaacttttg tcggagacgg agaagcggcc gttcatcgac   660
gaggctaagc ggctgcgagc gctgcacatg aaggagcacc cggattataa ataccggccc   720
cggcggaaaa ccaagacgct catgaagaag gataagtaca cgctgccggg cgggctgctg   780
gcccccggcg gcaatagcat ggcgagcggg gtcggggtgg gcgccggcct gggcgcgggc   840
gtgaaccagc gcatggacag ttacgcgcac atgaacggct ggagcaacgg cagctacagc   900
atgatgcagg accagctggg ctacccgcag cacccgggcc tcaatgcgca cggcgcagcg   960
cagatgcagc ccatgcaccg ctacgacgtg agcgccctgc agtacaactc catgaccagc  1020
tcgcagacct acatgaacgg ctcgcccacc tacagcatgt cctactcgca gcagggcacc  1080
cctggcatgg ctcttggctc catgggttcg gtggtcaagt ccgaggccag ctccagcccc  1140
cctgtggtta cctcttcctc ccactccagg gcgcccttgcc aggccgggga cctcggggac  1200
atgatcagca tgtatctccc cggcgccgag gtgccggaac ccgccgcccc cagcagactt  1260
cacatgtccc agcactacca gagcggcccg gtgcccggca cggccattaa cggcacactg  1320
cccctctcac acatgtga                                                1338
```

<210> SEQ ID NO 4
<211> LENGTH: 1467
<212> TYPE: DNA
<213> ORGANISM: artificial sequence
<220> FEATURE:
<223> OTHER INFORMATION: synthetic

<400> SEQUENCE: 4

| | | | | | |
|---|---|---|---|---|---|
| atgtacggtc | gtaaaaaacg | tcgtcagcgt | cgtcgtatgg | gtcatcacca | tcatcatcac | 60 |
| atggtgaaag | aactgcagga | aattcgtctg | gggtcggact | cagaagtcaa | tcaagaagct | 120 |
| aagccagagg | tcaagccaga | agtcaagcct | gagactcaca | tcaatttaaa | ggtgtccgat | 180 |
| ggatcttcag | agatcttctt | caagatcaaa | aagaccactc | ctttaagaag | gctgatggaa | 240 |
| gcgttcgcta | aaagacaggg | taaggaaatg | gactccttaa | gattcttgta | cgacggtatt | 300 |
| agaattcaag | ctgatcaggc | ccctgaagat | ttggacatgg | aggataacga | tattattgag | 360 |
| gctcatcgcg | aacagattgg | aggtatggcg | ggacacctgg | cttcggattt | cgccttctcg | 420 |
| ccccctccag | gtggtggagg | tgatgggcca | gggggccgg | agccgggctg | ggttgatcct | 480 |
| cggacctggc | taagcttcca | aggccctcct | ggagggccag | gaatcgggcc | ggggggttgg | 540 |
| ccaggctctg | aggtgtgggg | gattccccca | tgcccccgc | cgtatgagtt | ctgtggggg | 600 |
| atggcgtact | gtgggcccca | ggttggagtg | gggctagtgc | cccaaggcgg | cttggagacc | 660 |
| tctcagcctg | agggcgaagc | aggagtcggg | gtggagagca | actccgatgg | ggcctccccg | 720 |
| gagccctgca | ccgtcacccc | tggtgccgtg | aagctggaga | aggagaagct | ggagcaaaac | 780 |
| ccggaggagt | cccaggacat | caaagctctg | cagaaagaac | tcgagcaatt | gccaagctc | 840 |
| ctgaagcaga | gaggatcac | cctgggatat | acacaggccg | atgtggggct | caccctgggg | 900 |
| gttctatttg | ggaaggtatt | cagccaaacg | accatctgcc | gctttgaggc | tctgcagctt | 960 |
| agcttcaaga | acatgtgtaa | gctgcggccc | ttgctgcaga | agtgggtgga | ggaagctgac | 1020 |
| aacaatgaaa | atcttcagga | gatatgcaaa | gcagaaaccc | tcgtgcaggc | ccgaaagaga | 1080 |
| aagcgaacca | gtatcgagaa | ccgagtgaga | ggcaacctgg | agaatttgtt | cctgcagtgc | 1140 |
| ccgaaaccca | cactgcagca | gatcagccac | atcgcccagc | agcttgggct | cgagaaggat | 1200 |
| gtggtccgag | tgtggttctg | taaccggcgc | cagaagggca | agcgatcaag | cagcgactat | 1260 |
| gcacaacgag | aggattttga | ggctgctggg | tctcctttct | caggggggacc | agtgtccttt | 1320 |
| cctctggccc | cagggcccca | ttttggtacc | ccaggctatg | ggagcccctca | cttcactgca | 1380 |
| ctgtactcct | cggtcccttt | ccctgagggg | gaagcctttc | cccctgtctc | cgtcaccact | 1440 |
| ctgggctctc | ccatgcattc | aaactga | | | | 1467 |

<210> SEQ ID NO 5
<211> LENGTH: 1797
<212> TYPE: DNA
<213> ORGANISM: artificial sequence
<220> FEATURE:
<223> OTHER INFORMATION: synthetic

<400> SEQUENCE: 5

| | | | | | |
|---|---|---|---|---|---|
| atgtacggtc | gtaaaaaacg | tcgtcagcgt | cgtcgtatgg | gtcatcacca | tcatcatcac | 60 |
| atggtgaaag | aactgcagga | aattcgtctg | gggtcggact | cagaagtcaa | tcaagaagct | 120 |
| aagccagagg | tcaagccaga | agtcaagcct | gagactcaca | tcaatttaaa | ggtgtccgat | 180 |
| ggatcttcag | agatcttctt | caagatcaaa | aagaccactc | ctttaagaag | gctgatggaa | 240 |
| gcgttcgcta | aaagacaggg | taaggaaatg | gactccttaa | gattcttgta | cgacggtatt | 300 |

```
agaattcaag ctgatcaggc ccctgaagat ttggacatgg aggataacga tattattgag      360
gctcatcgcg aacagattgg aggtatggct gtcagcgacg cgctgctccc atctttctcc      420
acgttcgcgt ctggcccggc gggaagggag aagacactgc gtcaagcagg tgccccgaat      480
aaccgctggc gggaggagct ctcccacatg aagcgacttc ccccagtgct tcccggccgc      540
ccctatgacc tggcggcggc gaccgtggcc acagacctgg agagcggcgg agccggtgcg      600
gcttgcggcg gtagcaacct ggcgcccta cctcggagag agaccgagga gttcaacgat       660
ctcctggacc tggactttat tctctccaat tcgctgaccc atcctccgga gtcagtggcc      720
gccaccgtgt cctcgtcagc gtcagcctcc tcttcgtcgt cgccgtcgag cagcggccct      780
gccagcgcgc cctccacctg cagcttcacc tatccgatcc gggccgggaa cgacccgggc      840
gtggcgccgg gcggcacggg cggaggcctc ctctatggca gggagtccgc tcccctccg      900 acggctccct tcaacctggc ggacatcaac gacgtgagcc cctcgggcgg cttcgtggcc      960
gagctcctgc ggccagaatt ggacccggtg tacattccgc gcagcagcc gcagccgcca     1020 ggtggcgggc tgatgggcaa gttcgtgctg aaggcgtcgc tgagcgcccc tggcagcgag     1080
tacggcagcc cgtcggtcat cagcgtcagc aaaggcagcc ctgacggcag ccacccggtg     1140
gtggtggcgc cctacaacgg cgggccgccg cgcacgtgcc ccaagatcaa gcaggaggcg     1200
gtctcttcgt gcacccactt gggcgctgga ccccctctca gcaatggcca ccggccggct     1260
gcacacgact tcccctgggg gcggcagctc cccagcagga ctaccccgac cctgggtctt     1320
gaggaagtgc tgagcagcag ggactgtcac cctgccctgc cgcttcctcc cggcttccat     1380
ccccacccgg ggcccaatta cccatccttc ctgcccgatc agatgcagcc gcaagtcccg     1440
ccgctccatt accaagagct catgccaccc ggttcctgca tgccagagga gcccaagcca     1500 aagagggaa gacgatcgtg gccccggaaa aggaccgcca cccacacttg tgattacgcg      1560
ggctgcggca aaacctacac aaagagttcc catctcaagg cacacctgcg aacccacaca     1620
ggtgagaaac cttaccactg tgactgggac ggctgtggat ggaaattcgc ccgctcagat     1680
gaactgacca ggcactaccg taaacacacg gggcaccgcc cgttccagtg ccaaaaatgc     1740
gaccgagcat tttccaggtc ggaccactc gccttacaca tgaagaggca ttttttaa       1797
```

<210> SEQ ID NO 6
<211> LENGTH: 1704
<212> TYPE: DNA
<213> ORGANISM: artificial sequence
<220> FEATURE:
<223> OTHER INFORMATION: synthetic

<400> SEQUENCE: 6

```
atgtacggtc gtaaaaaacg tcgtcagcgt cgtcgtatgg gtcatcacca tcatcatcac       60
atggtgaaag aactgcagga aattcgtctg gggtcggact cagaagtcaa tcaagaagct      120
aagccagagg tcaagccaga agtcaagcct gagactcaca tcaatttaaa ggtgtccgat      180
ggatcttcag agatcttctt caagatcaaa aagaccactc ctttaagaag gctgatggaa      240
gcgttcgcta aaagacaggg taaggaaatg gactccttaa gattcttgta cgacggtatt      300
agaattcaag ctgatcaggc ccctgaagat ttggacatgg aggataacga tattattgag      360
gctcatcgcg aacagattgg aggtatgccc ctcaacgtta gcttcaccaa caggaactat      420
gacctcgact acgactcggt gcagccgtat ttctactgcg acgaggagga gaacttctac      480
cagcagcagc agcagagcga gctgcagccc cggcgcccca gcgaggatat ctggaagaaa      540
ttcgagctgc tgcccacccc gccccgtgtcc cctagccgcc gctccgggct ctgctcgccc      600
```

-continued

```
tcctacgttg cggtcacacc cttctcccct cggggagaca acgacggcgg tggcgggagc    660
ttctccacgg ccgaccagct ggagatggtg accgagctgc tgggaggaga catggtgaac    720
cagagtttca tctgcgaccc ggacgacgag accttcatca aaaacatcat catccaggac    780
tgtatgtgga gcggcttctc ggccgccgcc aagctcgtct cagagaagct ggcctcctac    840
caggctgcgc gcaaagacag cggcagcccg aaccccgccc gcggccacag cgtctgctcc    900
acctccagct tgtacctgca ggatctgagc gccgccgcct cagagtgcat cgacccctcg    960
gtggtcttcc cctaccctct caacgacagc agctcgccca gtcctgcgc ctcgcaagac    1020 tccagcgcct tctctccgtc ctcggattct ctgctctcct cgacggagtc ctccccgcag    1080
ggcagccccg agcccctggt gctccatgag gagacaccgc ccaccaccag cagcgactct    1140
gaggaggaac aagaagatga ggaagaaatc gatgttgttt ctgtggaaaa gaggcaggct    1200
cctggcaaaa ggtcagagtc tggatcacct tctgctggag ccacagcaa acctcctcac    1260 agcccactgg tcctcaagag gtgccacgtc tccacacatc agcacaacta cgcagcgcct    1320
ccctccactc ggaaggacta tcctgctgcc aagagggtca agttggacag tgtcagagtc    1380
ctgagacaga tcagcaacaa ccgaaaatgc accagcccca ggtcctcgga caccgaggag    1440
aatgtcaaga ggcgaacaca caacgtcttg gagcgccaga ggaggaacga gctaaaacgg    1500
agcttttttg ccctgcgtga ccagatcccg gagttggaaa acaatgaaaa ggcccccaag    1560
gtagttatcc ttaaaaaagc cacagcatac atcctgtccg tccaagcaga ggagcaaaag    1620
ctcatttctg aagaggactt gttgcggaaa cgacgagaac agttgaaaca caaacttgaa    1680
cagctacgga actcttgtgc gtaa                                          1704
```

<210> SEQ ID NO 7
<211> LENGTH: 78
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 7

```
cgacatatgt acggtcgtaa aaaacgtcgt cagcgtcgtc gtatgggtca tcaccatcat    60
catcacatgg tgaaagaa                                                  78
```

<210> SEQ ID NO 8
<211> LENGTH: 75
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 8

```
ctggcttagc ttcttgattg acttctgagt ccgaccccag acgaatttcc tgcagttctt    60
tcaccatgtg atgat                                                     75
```

<210> SEQ ID NO 9
<211> LENGTH: 75
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 9
caatcaagaa gctaagccag aggtcaagcc agaagtcaag cctgagactc acatcaattt    60
aaaggtgtcc gatgg                                                    75

<210> SEQ ID NO 10
<211> LENGTH: 75
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 10
catcagcctt cttaaaggag tggtcttttt gatcttgaag aagatctctg aagatccatc    60
ggacaccttt aaatt                                                    75

<210> SEQ ID NO 11
<211> LENGTH: 110
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 11
ctcctttaag aaggctgatg gaagcgttcg ctaaaagaca gggtaaggaa atggactcct    60
taagattctt gtacgacggt attagaattc aagctgatca ggcccctgaa              110

<210> SEQ ID NO 12
<211> LENGTH: 77
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 12
acctccaatc tgttcgcgat gagcctcaat aatatcgtta tcctccatgt ccaaatcttc    60
aggggcctga tcagctt                                                  77

<210> SEQ ID NO 13
<211> LENGTH: 41
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 13
atcgcgaaca gattggaggt atgcccctca acgttagctt c                       41

<210> SEQ ID NO 14
<211> LENGTH: 29
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 14
cgactcgagt tacgcacaag agttccgta                                     29

<210> SEQ ID NO 15
<211> LENGTH: 40
<212> TYPE: DNA
<213> ORGANISM: artificial sequence

```
<220> FEATURE:
<221> NAME/KEY: misc_feature
<223> OTHER INFORMATION: synthetic, primer

<400> SEQUENCE: 15
atcgcgaaca gattggaggt atggctgtca gcgacgcgct                          40

<210> SEQ ID NO 16
<211> LENGTH: 30
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 16
cgactcgagt taaaaatgcc tcttcatgtg                                     30

<210> SEQ ID NO 17
<211> LENGTH: 40
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 17
atcgcgaaca gattggaggt atgagtgtgg atccagcttg                          40

<210> SEQ ID NO 18
<211> LENGTH: 29
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 18
cgactcgagt cacacgtctt caggttgca                                      29

<210> SEQ ID NO 19
<211> LENGTH: 40
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 19
atcgcgaaca gattggaggt atggcgggac acctggcttc                          40

<210> SEQ ID NO 20
<211> LENGTH: 29
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 20
cgactcgagt cagtttgaat gcatgggag                                      29

<210> SEQ ID NO 21
<211> LENGTH: 66
<212> TYPE: DNA
<213> ORGANISM: artificial sequence
<220> FEATURE:
<221> NAME/KEY: misc_feature
```

```
<223> OTHER INFORMATION: synthetic, primer

<400> SEQUENCE: 21
catgcaaata tgcaaatatg caaatatgca aatatgcaaa tatgcaaata tgcaaatatg    60
caaata                                                               66

<210> SEQ ID NO 22
<211> LENGTH: 74
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 22
ctagaatgca aatatgcaaa tatgcaaata tgcaaatatg caaatatgca aatatgcaaa    60
tatgcaaatg gtac                                                      74

<210> SEQ ID NO 23
<211> LENGTH: 58
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 23
cagggtgcag ggtgcagggt gcagggtgca gggtgcaggg tgcagggtgc agggtgca      58

<210> SEQ ID NO 24
<211> LENGTH: 66
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 24
ctagagcacc ctgcaccctg caccctgcac cctgcaccct gcaccctgca ccctgcaccc    60
tggtac                                                               66

<210> SEQ ID NO 25
<211> LENGTH: 29
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 25
cgaggtaccg agttctctgt tctataaac                                      29

<210> SEQ ID NO 26
<211> LENGTH: 29
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 26
cgacccgggc ctctcgtggt ctgcacaga                                      29

<210> SEQ ID NO 27
<211> LENGTH: 120
```

-continued

```
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 27
ccggtaccgg gttgtggcag ccagtcacgt gcccgccgcg tagccacacc tctgctcctc       60
agagcaatgt caagcggtca cgtgtgatag caacagatca cgtggctgcc atcgccctc      120

<210> SEQ ID NO 28
<211> LENGTH: 117
<212> TYPE: DNA
<213> ORGANISM: artificial sequence
<220> FEATURE:
<221> NAME/KEY: misc_feature
<223> OTHER INFORMATION: synthetic, primer

<400> SEQUENCE: 28
atgaattccg gacgttctgg gcacgtgacc gccacccatg cgctgagggg cggacaggag       60
gtgcttcgac tgggaggagg gcgaagagtg taaggggggcg gaggggcgat ggcagcc       117
```

FUSION PROTEIN MIXTURE FOR INDUCING HUMAN PLURIPOTENT STEM CELL AND PREPARATION METHOD THERE OF

INCORPORATION BY REFERENCE OF SEQUENCE LISTING

The entirety of the Sequence Listing submitted at the same time of the filing of the instant application is incorporated by reference herein.

FIELD

The present invention relates to the technique of recombinant fusion protein, specifically relates to a protein mixture. In addition, the invention relates to a preparation method of the protein mixture.

BACKGROUND

Human Induced Pluripotent Stem (IPS) Cells

In 2006, Japanese Yamanaka laboratory successfully obtained a pluripotent stem cell, which was very similar to mouse embryonic stem cells in characteristics, by transducing four transcription factors (KLF4,c-Myc, SOX2, OCT-4) into mouse embryonic stem cells and adult fibroblast through retrovirus. Soon, using the same method, human fibroblast was transduced to induce human pluripotent stem cells successfully. Afterwards, a variety of IPS cells induced from patient cells with hereditary disease were obtained successfully. IPS cells are similar to embryonic stem cells in characteristics. The embryonic stem cells can differentiate into all types of somatic cells, which are able to be used to repair the tissue injury from diseases or hurt. So the embryonic stem cells have a very extensive application prospect in the field of regenerative medicine. However, application of embryonic stem cells in medicine has two important obstacles: one is immunologic rejection after transplantation, the other is the ethical consideration of using a human embryo. Even if the embryonic stem cells were obtained through somatic cell nuclear transfer, there are still ethical problems. Nevertheless, the human IPS cells can be obtained from patient cells, which does not have the problem of immunologic rejection. And since no human embryo is destroyed or human ootids are used, the ethical problem of using embryonic stem cells does not exist. These advantages above enable the IPS technology to have a better application prospect in regenerative medicine.

The Technology of Inducing Pluripotent Stem (IPS) Cells

Initially, inducing Pluripotent Stem cells needed to use replication-deficient retrovirus or Lentiviral Vector, which could transduce the reprogramming factors into cells. These viral vectors would integrate into genome of the host cell. Although these exogenous genes are silent in IPS cells at most cases, once being reactivated, they will induce tumor. Leaked expression of these genes also possibly enables IPS cells to differentiate and ripe incompletely, resulting in the increasing risk of forming immaturity teratoma. Viral integration also possibly activates or terminates expression of endogenous genes. In the history of gene therapy, using the technology of retrovirus integration resulted in leukemia because of activating oncogenes. Many laboratories tried to use the technology of non-viral integration to induce Pluripotent Stem cells. Adenovirus and/or plasmid were used as vectors to introduce reprogramming factors into cells, thus obtained IPS cells successfully. But the rate of obtaining IPS cells was very low. OriP/EBNA-1 plasmid episome was used as vector to induce IPS cells. Some laboratories used Cre/loxp, transposon/transposase, to remove the exogenous gene being integrated into genome after obtaining IPS cells. Another method to avoid integration of exogenous genes was to replace reprogramming factors by chemicals. So far, from the results published, no completely alternative reprogramming transcription chemicals or combination has been found, only one or two reprogramming factors could be replaced. Even though no foreign gene was integrated into IPS cells, the method mentioned above could not completely avoid genomic change, for instance, the method of plasmid transformation would bring genomic integration with low chance, while chemicals could lead to gene mutation.

Protein Transduction

Initially, protein transduction was originated from the research of HIV TAT protein. People found that the entire HIV TAT protein could enter cells to activate transduction of viral gene. Further studies showed that a region (TAT PTD) of HIV TAT protein was responsible for the function of entering cells. Coupling or fusion of TAT PTD and macromolecules was found useful for the macromolecules to enter cell. Study showed arginine with positive charges was necessary for TAT PTD to enter cytoplasm through cell membrane. Any mutation of an arginine would lead to loss of the transduction function. Based on this, polyarginine was found to possess the function of transduction similarly. The technology of protein transduction by TAT PTD or the other protein transducing peptide has a great potential for macromolecular pharmaceuticals to enter cells and exert their function.

Cleavage of SUMO Fusion Proteins

Small ubiquitin-like modifier (SUMO) could covalently modify protein. SUMO modification can regulate various cell process including nuclear transfer, signal transduction and stability of protein. Ulp1, a SUMO protease, could specifically recognize the tertiary structure of SUMO, and cleave at the joint of SUMO and its modified protein. When SUMO fusing with other protein (equivalently SUMO modifies N-terminal amino of target protein), Ulp1 could specifically remove SUMO, and release the target protein completely.

Protein Inducing Pluripotent Stem Cells

The reprogramming factors (KLF4, c-Myc, SOX2, OCT-4) were introduced into cells by the technology of protein transduction, which can avoid the security problems mentioned above. A laboratory of Scripps institute successfully obtained mouse IPS cells by a recombinant protein of four reprogramming factors expressed in E. coli, with the addition of a kind of chemical (HDAC inhibitor). The recombinant reprogramming factors used in the laboratory were OCT-4, KLF4, Sox2, c-Myc. The four reprogramming factors were introduced into cells by polyarginine with C-terminal fusion. The technology can completely overcome all disadvantages when the reprogramming factors were introduced into cells by using DNA, thus enables the possible application of IPS cells in Regenerative Medicine to take a significant step forward. However, the protein transduction peptide—polyarginine fused the reprogramming factors directly. Since the transduction peptide carried strong positive charges, which possibly nonspecifically bind with genomic DNA carrying negative charges, thus the transcription factor fused with transduction peptide could nonspecifically change gene expression. The nonspecific change of gene expression could lead to low rate of inducing Pluripotent Stem Cells or some permanent change of gene expression, thus influenced subsequent differentiation and maturity of the IPS cells. Hence, obtaining a preparation, which could overcome the disadvantages above in inducing Pluripotent Stem Cells, had a great significance for human IPS cells to use practically in Regenerative Medicine.

DETAILED DESCRIPTION

Figure 1:
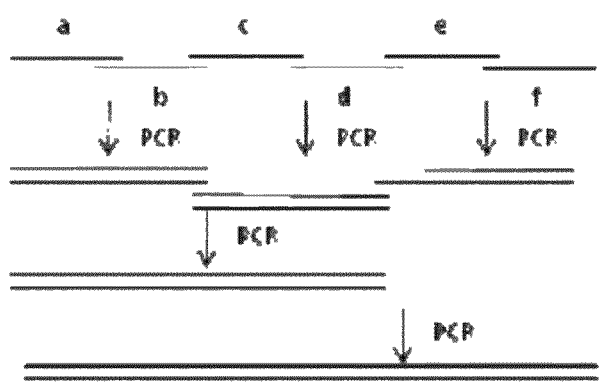
FIG. 1 is a schematic diagram illustrating PCR reaction for constructing of PTD-NES-SUMO in accordance with Example 1 of the present invention.

The technical problem to be solved in this invention is to provide a protein mixture with potential value of medical application. The protein mixture can greatly decrease the possibility of nonspecifically combining with genomic DNA, which has activity of transcription activation after being transduced into cells. It can be used to induce Pluripotent Stem Cells. Moreover, the invention provides a method for preparing the protein mixture.

In order to solve the technical problems mentioned above, the invention provides the following technical solutions:

The invention provides a protein mixture, which consists of a fusion protein of C-myc, SOX2, KLF4 and OCT-4. The applied concentration for each fusion protein is ing/ml-1 mg/m. The fusion proteins comprise the structure: PTD-SUMO-Protein, wherein, PTD is a Protein Transduction Domain, standing for HIV-TAT, HSV-VP22, AntP or polyarginine; SUMO is a small ubiquitin-like modifier, standing for yeast SMT3p or its homologs in other species, which is the recognizing region after the fusion protein enters cells and is cleaved; Protein is C-myc, SOX2, KLF4 or OCT-4.

Protein mentioned above is TAT PTD region of HIV TAT protein, or other amino acid sequences with protein transduction function. The Protein Transduction Domain (PTD) enables the protein mixture to enter human cells.

Small ubiquitin-like modifier (SUMO) mentioned above is yeast SMT3p or other amino acid sequences, whose tertiary structure can be recognized and cleaved by SUMO protease. The small ubiquitin-like modifier (SUMO) enables the protein transduction peptide to be removed from the fusion protein.

Preferably, NES is inserted between the mentioned PTD and SUMO. The mentioned fusion protein has the structure: PTD-NES-SUMO-Protein, NES is an optional Nuclear Export Sequence, which decides cytoplasmic localization of the fusion protein.

The mentioned optional Nuclear Export Sequence is human IkBa Nuclear Export Sequence, or the amino acid sequences with function of Nuclear Export Sequence.

The mentioned PTD-NES-SUMO has DNA sequence as shown in SEQ ID NO.1, and has amino acid sequence as shown in SEQ ID NO.2.

The mentioned PTD-NES-SUMO-SOX2 has DNA coding sequence as shown in SEQ ID NO.3, PTD-NES-SUMO-OCT-4 has DNA coding sequence as shown in SEQ ID NO.4, PTD-NES-SUMO-KLF4 has DNA coding sequence as shown in SEQ ID NO.5, PTD-NES-SUMO-C-myc has DNA coding sequence as showed in SEQ ID NO.6.

Preferably, 6 histidines are inserted between PTD and NES for purification.

In addition, the invention provides a preparation method of the protein mixture, including the following steps:

(1) Constructing the expression plasmid of PTD-NES-SUMO-Protein: First, respectively synthesize 8 oligo primers which are 75 bp in length and mutually overlap in 20 bp. After three times of overlapping PCR, PTD-NES-SUMO is synthesized. Then, human OCT-4, SOX2, KLF4, C-myc cDNA are obtained from amplification of total RNA of human embryonic stem cells, whose 3'-end has an XhoI site, which were assembled by PCR with the synthesized TAT-NES-SUMO sequence. The product is cloned in NdeI/XhoI site of pET-24a (+) vector.

(2) Screening the expression strain: PTD-NES-SUMO-Protein expression plasmid obtained from the step 1 is transformed into host strain BL21, to culture and screen high-expression clone with mini-scale.

(3) Large-scale expression of the fusion protein: the expression strain is inoculated in flasks, and cultured until OD 0.6, then IPTG is added to induce for 3 hours.

(4) Separation and purification of the fusion protein: the fusion protein mentioned above is separated and purified by hydrophobic chromatography and ion exchange chromatography.

The protein mixture prepared by the invention, can fundamentally solve the present technology deficiencies (the non-specific change of gene expression could lead to low rate of inducing Pluripotent Stem Cells or some permanent change of gene expression, thus influenced subsequent differentiation and maturity of the IPS cells). The fusion of PTD enables the fusion protein to enter cells. SUMO in the fusion protein enables protein transduction peptide to be cleaved from the fusion protein, to remove the fused PTD, NES, SUMO. If the mixture is used to induce Pluripotent Stem Cells, it can minimize the adverse effects brought by adding inducer for obtaining IPS cells during the course of inducing Pluripotent Stem cells, which adapts the IPS cells for application in regeneration medicine and other related fields.

The invention will be explained below in closer detail by reference to the schematic drawings and examples. Although the present invention has been described in detail, it should be understood that various changes, substitutions and alternations can be made hereto without departing from the spirit and scope of the invention. The experimental methods without detailed conditions mentioned should be conducted following the routine conditions, for example: conditions listed in the laboratory handbook: Sambrook et al., molecular clone: (New York: Cold Spring Harbor Laboratory Press, 1989), or according to the instructions advised by manufacturers.

EXAMPLE 1

Preparation of the Protein Mixture

1. Constructing the Expression Plasmid of TAT-NES-SUMO—Reprogramming Factors

The codons of HIV TAT PTD, yeast SMT3p (SUMO) and human IkBa Nuclea Export Sequence (NES) are optimized according to the amino acid sequence listed in prior literatures, for the purpose of high-level expression in *E. coli*. TAT-NES-SMT3p are arranged in sequence, and 6 histidines are inserted between TAT and NES for purification. Encoding sequences of this part of fusion protein are synthesized by PCR assembling based on oligonucleotide, and a NdeI site is at its 5'-end. The methods are as follow: synthesize respectively 6 oligo primers which are 75 bp in length and mutually overlap in 20 bp. After three times of overlapping PCR (as shown in FIG. 1), first step: respectively mix primer a (the sequence shown as SEQ ID NO.7) and primer b (the sequence shown as SEQ ID NO.8); primer c (the sequence shown as SEQ ID NO.9) and primer d (the sequence showed as SEQ ID NO.10); primer e (the sequence showed as SEQ ID NO.11) and primer f (the sequence showed as SEQ ID NO.12), to perform PCR reactions, then get the products: ab, cd, ef; second step: mix the primer a, d with the PCR products ab, cd from the last cycle, then perform PCR amplification; third step: mix primer a, f and the PCR product ad from the last cycle, and the product of from the first cycle, then perform PCR amplification, to get the product af. Separate the amplification products by agarose gel electrophoresis, then recover the target band. The reaction system (high fidelity-amplification system, Roche) is prepared following the manufacture's instruction. The reaction conditions are: first step: 95° C., 5 minutes; second step: 94° C., 45 seconds, 55° C. 45 seconds, 72° C. 55 seconds, 30 cycles; third step: 72° C. 7 minutes.

Use Invitrogen Trizol Reagent to extract the total RNA from 5×106 human embryonic stem cells. According to the instruction (Invitrogen) of Superscript III reverse transcription PCR kit, RNA is reverse transcribed into cDNA using random primer. cDNA of OCT-4, SOX2, KLF4, C-myc are obtained by amplification using the following primers:

```
C-myc 5'
                                        (SEQ ID NO. 13)
ATCGCGAACAGATTGGAGGTATGCCCCTCAACGTTAGCTTC C-myc 3'
                                        (SEQ ID NO. 14)
CGACTCGAGTTACGCACAAGAGTTCCGTA Klf4 5'
                                        (SEQ ID NO. 15)
ATCGCGAACAGATTGGAGGTATGGCTGTCAGCGACGCGCT Klf4 3'
                                        (SEQ ID NO. 16)
CGACTCGAGTTAAAAATGCCTCTTCATGTG Nanog 5'
                                        (SEQ ID NO. 17)
ATCGCGAACAGATTGGAGGTATGAGTGTGGATCCAGCTTG Nanog 3'
                                        (SEQ ID NO. 18)
CGACTCGAGTCACACGTCTTCAGGTTGCA Oct-4 5'
                                        (SEQ ID NO. 19)
ATCGCGAACAGATTGGAGGTATGGCGGGACACCTGGCTTC Oct-4 3'
                                        (SEQ ID NO. 20)
CGACTCGAGTCAGTTTGAATGCATGGGAG
```

In these primers, all their 5'-end contain 20 bases being the same as the 3'-end of TAT-NES-SMT3p fragment, which is convenient for assembling.

Each cDNA is assembled with the synthetic TAT-NES-SUMO sequence by PCR (the reaction conditions are same as those for assembling TAT-NES-SUMO, using primer a and 3' primer of each cDNA). The product is cloned into vector pET-24a(+) (Novagen) at NdeI/XhoI site.

TAT-NES-SUMO has DNA coding sequence shown in SEQ ID NO.1.
TAT-NES-SUMO has amino acid sequence shown in SEQ ID NO.2.
TAT-NES-SUMO-50×2 has DNA coding sequence shown in SEQ ID NO.3.
TAT-NES-SUMO-OCT-4 has DNA coding sequence shown in SEQ ID NO.4,
TAT-NES-SUMO-KLF4 has DNA coding sequence shown in SEQ ID NO.5,
TAT-NES-SUMO-C-myc has DNA coding sequence shown in SEQ ID NO.6

2. Screening Expression Strains

The fusion expression plasmid is transformed into host strain BL21 (DE3). Screen high-expression clone by mini-scale culture. In 3 ml *E. coli* of OD 0.6, 0.1 mM IPTG is added to induce expression for 3 hours. The thalli are collected and sampling buffer is added to boil for 5 minutes. Then SDS polyacrylamide gel electrophoresis and Coomassie Brilliant Blue Stain are used, select high-expression clone as seed for large-scale expression. By further analysis on the high-expression strain, most of the expressed fusion protein is found in inclusion bodies.

3. Large-Scale Expression of the Fusion Protein

The expression strain is inoculated in 10 L LB media, cultured at 37° C. till OD600 0.6, then 0.1M IPTG is added to induce for 3 hours. Then the concentration reaches OD600 1.0.

The cultures above are centrifuged to remove media, and get about 27.4 g thalli. 300 ml lysis buffer (50 mM PH 8.0 Tris-Cl, 500 mM NaCl) is added to resuspend the thalli. Then the thalli are split using ultrasonic at 4° C., then centrifuged at 6000 rpm in low temperature, to remove supernatant. 300 ml lysis buffer is used to wash the precipitation, centrifuge; remove supernatant. Dissolve the inclusion bodies with solubilized buffer (50 mM PH 8.0 Tris-Cl, 500 mM NaCl, 8M Urea). After the inclusion bodies are dissolved, affinity chromatography is performed for purification through IMAC. After sample-loading, rinse solution (8M Urea, 500 mM NaCl, 50 mM Tris-HCl pH8.0, 20 mM Imidazole) is used to wash the components combined nonspecifically. Then (8M Urea PH 8.0 50 mM Tris-Hcl, 500 mM NaCl 250 mM Imidazole) is used to elute, meanwhile detecting 280 nM ultraviolet absorbance. The protein peak is collected. 80 ml eluent is obtained in all.

Hydrophobic chromatography. Solid NaCl is added in the elution buffer above to 2M, dissolved fully, centrifuges at 1000 RPM for 15 minutes and discards the pellet. The supernatant is loaded onto Phenyl Sepharose FF column equilibrated fully by equilibration buffer (2M NaCl, 50 mM Tris-HCl pH8.0). After loading, 3 column volumes of equilibration buffer is used to rinse, the target peak is eluted by elution buffer (50 mM Tris-HCl pH8.0).

The target protein is regulated to pH6.0 with 1M acetic acid, and diluted threefold with pyrogen-free water, which is loaded onto SP-HP column equilibrated fully with equilibration buffer (10 mM NaAc—HAc, pH6.0). Eluted with gradually-increasing NaCl concentration, the target protein collected is purified fusion protein. After filtration sterilization through 0.22 nm microfiltration membrane, it goes to functional detection.

EXAMPLE 2

Transduction Experiment of the Fusion Protein

Hela cells are cultured in high-glucose DMEM (10% fetal calf serum). When the cells overspread 30%, TAT-NES-SUMO-reprogramming factors are added (concentration of every protein is 5 ug/ml). After 12 hours, change the culture medium and continue to culture for 12 h, 24 h, 72 h. Wash cells with cold PBS two times. Split the cells with lysis buffer (PH 7.5 20 mM Tris-Cl, 200 mM NaCl, 1% NP-40, 1 mM PMSF). Cell lysis buffer with 40 ug total protein is added 5× sample-buffer and goes to SDS polyacrylamide gel electrophoresis, then it is transferred to PVDF membrane. Anti-OCT4, SOX2, c-Myc, (cell signaling) KLF4 (santa Cruz) are used in Western blot experiment.

Figure 2:
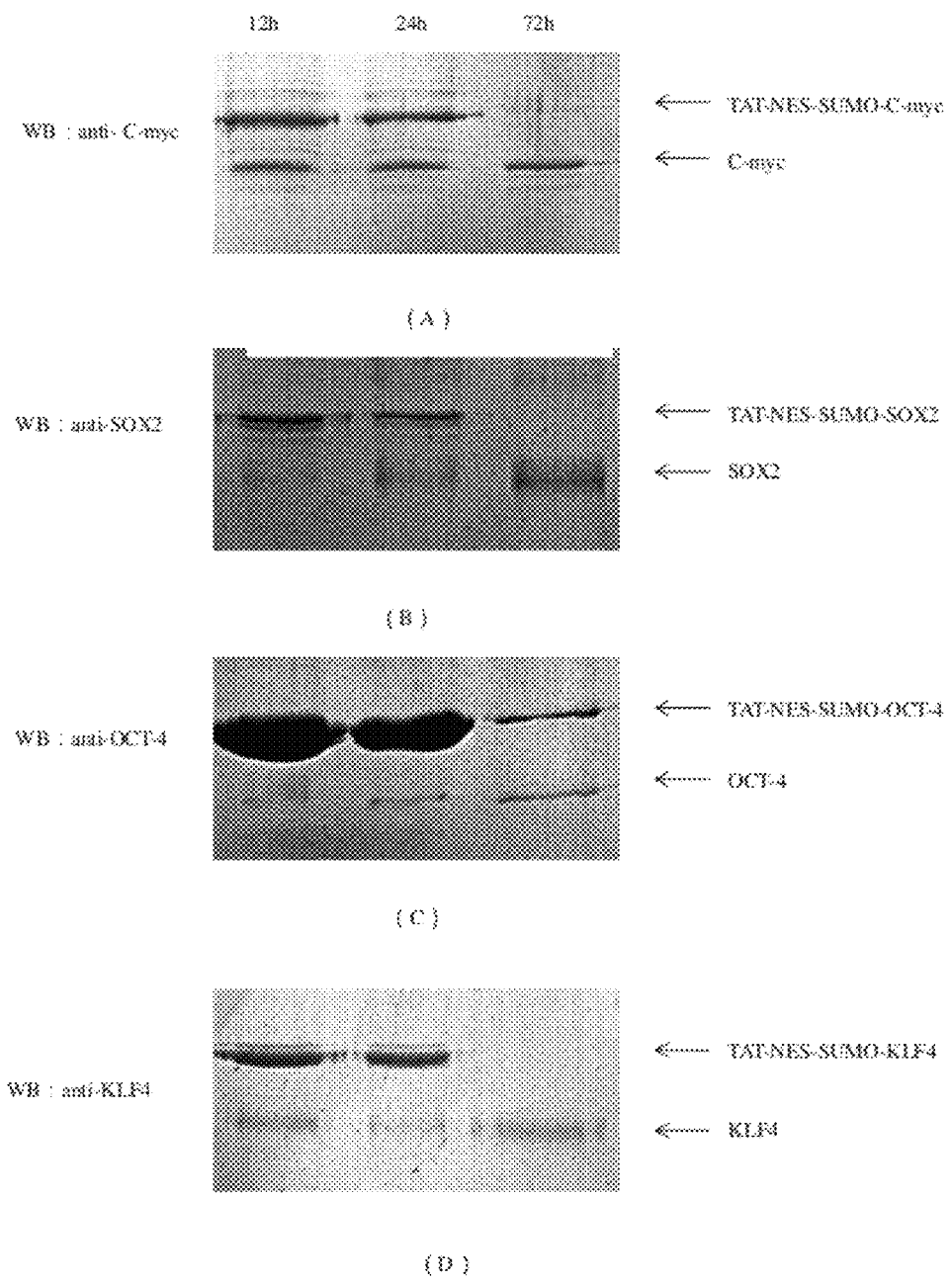
FIG. 2 is a schematic diagram illustrating the transduction experiment and intracellular cleavage of the fusion protein (using the method of western immunoblotting in accordance with Example 2 of the present invention, (A) the fusion protein TAT-NES-SUMO-C-myc, (B) the fusion protein TAT-NES-SUMO-SOX2, (C) the fusion protein TAT-NES-SUMO-OCT-4, (D) the fusion protein TAT-NES-SUMO-KLF4.

Results indicates (showed in FIG. 2): The fusion protein of the present invention can enter cells.

EXAMPLE 3

Intracellular Cleavage of the Fusion Protein

The experimental course is same as that in example 2. Results indicates (shown in FIG. 2) that the fusion protein can be cleaved intracellularly, so that it can reduce the nonspecific transcription changes due to DNA-binding activity of fused transduction region.

EXAMPLE 4

Intercellular Activity of the Fusion Protein

Construction of Luciferase Reporter Gene

OCT4 reporter gene plasmid: 8 tandem OCT4 binding sites (ATGCAAAT) Primer A (SEQ ID NO.21) primer B (SEQ ID NO.22) anneal, and are inserted in KpnI/BglII site of PGL3-promoter luciferase plasmid.

KLF4 reporter gene plasmid: 8 tandem KLF4 binding sites (AGGGTGC). Primer A (SEQ ID NO.23) primer B (SEQ ID NO.24) anneal, and are inserted in KpnI/BglII site of PGL3-promoter luciferase plasmid.

Sox2 reporter gene plasmid: Hesx1 gene. In the upstream 570-bp of Hesx1 translation initiation sites, PCR fragment is inserted into KpnI/SmaI site of pGL3-basic vector (Promega) by KpnI restriction digestion. Primer 5'-CGAGGTAC-CGAGTTCTCTGTTCTATAAAC-3'(SEQ ID NO.25) and 5'-CGACCCGGGCCTCTCGTGGTCTGCACAGA-3' (SEQ ID NO.26).

C-myc reporter gene plasmid: Primer A (5'-CCGGTAC-CGG GTTGTGGCAG CCAGTCACGT GCCCGCCGCG TAGCCACACC TCTGCTCCTC AGAGCAATGT CAAGCGGTCA CGTGTGATAG CAACAGATCA CGTG-GCTGCC ATCGCCCTC-3') (SEQ ID NO.27) and primer B (5'-ATGAATTCCG GACGTTCTGG GCACGTGACC GCCACCCATG CGCTGAGGGG CGGACAGGAG GTGCTTCGAC TGGGAGGAGG GCGAAGAGTG TAAGGGGGCG GAGGGGCGAT GGCAGCC-3') (SEQ ID NO.28) anneal, and are inserted into KpnI/SmaI site of PGL3-promoter luciferase plasmid by KpnI restriction digestion.

When Hela cells are cultured to overspread 50%, in the 12-well cell plate, fugene6 (from Roche) is used to transfect transcription reporter gene (firefly luciferase) and reference reporter plasmid pRL-TK-luc (promega, *Renilla luciferase*) of the reprogramming factors. After transfecting 6 hours, change media, add 5 ug/ml fusion protein. Then continue to culture till 12 h, 24 h, 48 h, 72 h. Wash cells with cold PBS, split cells with reporter lysis buffer (from promega). Luciferase activity of the cell lysis buffer is detected with dual-luciferase kit from Promega.

Figure 3:
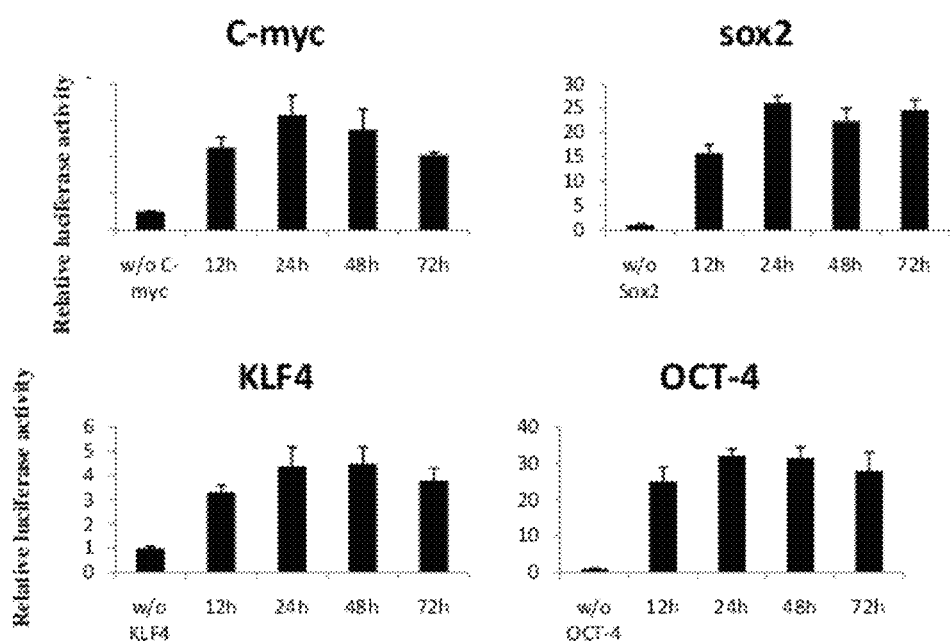
FIG. 3 is a schematic diagram illustrating the transcription activity of the fusion protein in accordance with Example 3 of the present invention.

Results indicated (showed in FIG. 3), 12 hours after adding the fusion protein into media, luciferase activity of the reporter gene greatly increases, till 72 h. It is indicated that the fusion protein possesses activity of transcriptional activation after being transducted into cells. The protein mixture of the invention can be used to induce Pluripotent Stem cells, it has a great application prospects in the field of regenerative medicine.

The invention claimed is:

1. A mixture comprising fusion proteins,
wherein each of the fusion proteins comprises the structure: PTD-NES-SUMO-Specific Protein, in that specific order;
wherein the PTD is a Protein Transduction Domain, and wherein the PTD is the TAT PTD region of HIV TAT;
wherein the NES is a Nuclear Export Sequence, and wherein the NES is human IkBa Nuclear Export Sequence;
wherein the SUMO is small ubiquitin-like modifier, wherein the SUMO is yeast SMT3p;
wherein the Specific Protein is any one of the proteins selected from the group consisting of C-myc, SOX2, KLF4 or OCT-4;
wherein the PTD-NES-SUMO moiety of the fusion protein is encoded by a polynucleotide comprising the nucleotide sequence of SEQ ID NO: 1; and
wherein an applied concentration of each of the fusion proteins in the mixture is 1 ng/ml-1 mg/ml.

2. The mixture of claim 1, wherein the SUMO is a cleavage site and enables the PTD to be cleaved from the fusion protein.

3. The mixture of claim 1, wherein the Specific Protein is SOX2, and the fusion protein is encoded by a polynucleotide comprising the nucleotide sequence of SEQ ID NO: 3.

4. The mixture of claim 1, wherein the PTD-NES-SUMO moiety of the fusion protein comprises the amino acid sequence of SEQ ID NO: 2.

5. The mixture of claim 1, wherein the Specific Protein is OCT4 and the fusion protein is encoded by a polynucleotide comprising the nucleotide sequence of SEQ ID NO: 4.

6. The mixture of claim 1, wherein the Specific Protein is KLF4 and the fusion protein is encoded by a polynucleotide comprising the nucleotide sequence of SEQ ID NO: 5.

7. The mixture of claim 1, wherein the Specific Protein is C-myc and the fusion protein is encoded by a polynucleotide comprising the nucleotide sequence of SEQ ID NO: 6.

8. A method for preparing a mixture of fusion proteins, wherein the method comprises the following steps:
(1) constructing an expression plasmid encoding a fusion protein comprising the structure PTD-NES-SUMO-Specific Protein, wherein:

PTD is a protein transduction domain and is the TAT PTD region of HIV-TAT,
NES is a Nuclear Export Sequence and is human IkBa Nuclear Export Sequence,
SUMO is small ubiquitin-like modifier and is yeast SMT3p, and
Specific Protein is selected from the group consisting of OCT-4, SOX2, KLF4, and C-myc,
wherein constructing the expression plasmid comprises:
synthesizing a polynucleotide encoding the PTD-NES-SUMO moiety of the fusion protein by synthesizing 8 oligo primers which are 75 base pairs in length and mutually overlap in 20 base pairs and performing overlapping PCR three times;
synthesizing a polynucleotide encoding the fusion protein by amplifying OCT-4, SOX2, KLF4, or C-myc cDNA from total RNA of human embryonic stem cells, whose 3'-end has an XhoI site and assembling the polynucleotide encoding the PTD-NES-SUMO-Specific Protein by PCR with the synthesized PTD-NES-SUMO encoding sequence, wherein said PTD-NES-SUMO encoding sequence comprises the nucleotide sequence of SEQ ID NO: 1; and
cloning the polynucleotide encoding the fusion protein into the NdeI/XhoI site of pET-24a(+) vector;
(2) screening an expression strain by:
transforming host strain BL21 with the expression plasmid from step (1);
and, screening for a clone that expresses the fusion protein;
(3) performing large-scale expression of the fusion protein by:
inoculating a culture medium with the clone that expresses the fusion protein and culturing until OD 0.6 followed by addition of IPTG and induction for 3 hours; and
(4) separating and purifying the fusion protein by hydrophobic chromatography and ion exchange chromatography.

* * * * *